United States Patent
Hu

(10) Patent No.: US 10,239,821 B2
(45) Date of Patent: Mar. 26, 2019

(54) PROCESS FOR THE CO-PRODUCTION OF LONG CHAIN AMINO ACIDS AND DIBASIC ACIDS

(71) Applicant: XIRUI TECHNOLOGY (BEIJING) CO., LTD, Beijing (CN)

(72) Inventor: Songzhou Hu, Princeton, NJ (US)

(73) Assignee: VITAWORKS IP, LLC, North Brunswick, NJ (US)

( * ) Notice: Subject to any disclaimer, the term of this patent is extended or adjusted under 35 U.S.C. 154(b) by 0 days.

(21) Appl. No.: 15/601,556

(22) PCT Filed: Dec. 17, 2015

(86) PCT No.: PCT/CN2015/097705
§ 371 (c)(1),
(2) Date: Aug. 7, 2018

(87) PCT Pub. No.: WO2017/088218
PCT Pub. Date: Jun. 1, 2017

(65) Prior Publication Data
US 2019/0016668 A1     Jan. 17, 2019

(30) Foreign Application Priority Data

Nov. 27, 2015    (CN) .......................... 2015 1 0848578

(51) Int. Cl.
| | | |
|---|---|---|
| *C07C 227/06* | (2006.01) | |
| *C07C 227/18* | (2006.01) | |
| *C07C 51/06* | (2006.01) | |
| *C07C 231/10* | (2006.01) | |
| *C07C 249/08* | (2006.01) | |

(52) U.S. Cl.
CPC ............ *C07C 227/06* (2013.01); *C07C 51/06* (2013.01); *C07C 227/18* (2013.01); *C07C 231/10* (2013.01); *C07C 249/08* (2013.01)

(58) Field of Classification Search
CPC ..... C07C 227/06; C07C 51/06; C07C 249/08; C07C 231/10
See application file for complete search history.

(56) References Cited

U.S. PATENT DOCUMENTS

| | | |
|---|---|---|
| 2,462,855 A | 3/1949 | Genas |
| 5,498,733 A | 3/1996 | Ayorinde |
| 6,218,574 B1 | 4/2001 | Liu et al. |
| 8,431,728 B2 | 4/2013 | Pees |
| 8,729,298 B2 | 5/2014 | Zang et al. |

FOREIGN PATENT DOCUMENTS

| | | |
|---|---|---|
| CN | 102329224 A | 1/2012 |
| CN | 102476990 A | 5/2012 |
| CN | 102795989 A | 11/2012 |
| CN | 103497100 A | 1/2014 |
| CN | 104447274 A | 3/2015 |
| CN | 104447280 A | 3/2015 |
| CN | 104496793 A | 4/2015 |
| CN | 104529741 A | 4/2015 |
| CN | 104529747 A | 4/2015 |
| CN | 104591998 A | 8/2016 |

OTHER PUBLICATIONS

A. Chauvel & G. Lefebvre, Petrochemical Processes 2: Major Oxygenated, Chlorinated and Nitrated Derivatives, pp. 274-286).
W. L. Kohlhase, E.H. Pryde, & J.C. Cowan, J. Am. Oil Chemists Soc., 1970, vol. 47, pp. 183-188.
Perkins, R.B., Roden, J.J. & Pryde, E.H.; Nylon-9 from unsaturated fatty derivatives: Preparation and characterization; J Am Oil Chem Soc (1975) vol. 52: No. 11, pp. 473-477. doi:10.1007/BF02637493.

*Primary Examiner* — Yevgeny Valenrod
*Assistant Examiner* — Blaine G Doletski
(74) *Attorney, Agent, or Firm* — Myers Wolin, LLC

(57) ABSTRACT

There is disclosed a process for the co-production of long chain ω-amino acid and long chain dibasic acid, comprising: (1) reacting long chain ketoacid derivative with hydroxylamine or subjecting ketoacid derivative to an ammoximation to yield oxime derivative; (2) subjecting oxime derivative to Beckmann rearrangement to yield a mixture of mixed amide derivatives; (3) hydrolyzing the mixed amide derivatives to produce long chain ω-amino acid and long chain dibasic acid.

10 Claims, No Drawings

PROCESS FOR THE CO-PRODUCTION OF LONG CHAIN AMINO ACIDS AND DIBASIC ACIDS

CROSS REFERENCE TO RELATED APPLICATIONS

This application is the U.S. national phase of International Application PCT/CN2015/097705, filed on Nov. 27, 2015, the entire contents of which are incorporated herein by reference.

TECHNICAL FIELD

The present invention relates to a method for the production of monomers for long chain nylons, more specifically, it relates to a process for the co-production of long chain ω-amino acids and dibasic acids.

BACKGROUNDS OF THE INVENTION

Long chain saturated aliphatic ω-amino acids, lactams, and dibasic acids are important monomers for long chain nylons and engineering plastics. Nylons are a class of polymers that contain amide bond on their backbone of chains. Nylons are one of the most widely used, most numerous in types, and most consumed class of engineering plastics.

Because of their unusual molecular structure, long chain nylons possess extraordinary physical properties, i.e., higher mechanical strength than metal, low hygroscopicity, excellent resistance to oil, low temperature, abrasion, and chemical corrosion, and most importantly, easy to fabricate. Long chain nylons are made into many kinds of plastics products, spun to fibers, and stretched to thin films. Long chain nylons are also used in paintings and hot melt adhesives. Hence, long chain nylons find wide applications in automobile, electrical, electronic, telecommunications, petrochemical, and aerospace industries.

Long chain ω-amino acids and lactams are used industrially as monomers to produce nylon-9, nylon-11, and nylon-12.

Long chain dibasic acids are condensed with diamines industrially as starting materials to produce nylon-610, nylon-612, nylon-510, nylon-512, nylon-1010, and nylon-1212.

Among the current production technologies, the nylon-9 monomer, 9-aminononanoic acid is produced from oleic acid or oleonitrile by a series of chemical reactions (details are described in J. Am. Oil Chemist's Soc., 1975, Vol. 52, No. 11, pp 473-477).

For the nylon-11 monomer, 11-aminoundecanoic acid, is produced from castor oil through ester exchange with methanol, pyrolysis at high-temperature, free radical addition of anhydrous hydrogen bromide, and finally ammonolysis (detailed process is described by A. Chauvel & G. Lefebvfre, Petrochemical Processes 2: Major Oxygenated, Chlorinated and Nitrated Derivatives, pp 274-278). The overall yield is not more than 55%.

The monomer of nylon-12, laurolactam, is produced from 1,3-butadiene through a series of reactions, i.e., trimerization to cyclododecatriene, hydrogenation to cyclododecane, oxidation to cyclododecanol or cyclododecanone, oximation, and Beckmann rearrangement (detailed process is described by A. Chauvel & G. Lefebvfre, Petrochemical Processes 2: Major Oxygenated, Chlorinated and Nitrated Derivatives, pp 279-286).

In the industrial production of long chain dibasic acids, azelaic acid is produced from oleic acid by oxidation, while sebacic acid is produced by alkaline scission of castor oil or derivatives at high temperature (200° C. to 250° C.), followed by purification and refining.

For the important dodecanedioic acid, there are two industrial processes of quite different nature. One is the chemical synthesis from 1,3-butadiene through catalyzed trimerization to cyclododecatriene, hydrogenation to cyclododecane, oxidation to cyclododecanol or cyclododecanone, and finally, oxidation by nitric acid. The other process is more preferable, i.e., biochemical oxidation of terminal methyl groups of high purity dodecane or lauric acid by fermentation.

In the production of these monomers by chemical synthesis, there exist problems for the current industrial processes, e.g., low overall yield (35% for 9-aminononanoic acid, 55% for 11-aminoundecanoic acid, 80% for sebacic acid), reaction conditions that are inherently dangerous and difficult to control. For example, the production of 9-aminononanoic acid requires the use of ozone, and the production of 11-aminoundecanoic acid requires a pyrolysis reaction at high temperature. Moreover, the production of laurolactam and dodecanedioic acid makes use of trimerization of 1,3-butadiene under inert reaction conditions with a flammable catalyst, while the production of sebacic acid requires a very corrosive alkaline scission of castor oil.

Although the reaction conditions are mild, fermentative oxidation of long chain alkanes or lauric acid via fermentation to produce dodecanedioic acid or other long chain dibasic acids, yields a crude product that contains a large amount of biomaterials and degraded short chain dibasic acids. To obtain a product suitable for the production of nylons, crude product must be subjected to complicated purification and refinement. Many methods to refine and purify the crude products are described in the literature. Detailed processes are disclosed in U.S. Pat. No. 6,218,574; U.S. Pat. No. 8,729,298; CN 104591998A; CN 102476990A; CN 102329224A; CN 103497100A; CN 102795989A; CN 104447274A; CN 104447280A; CN 104496793A; CN 104529741A; CN 104529747A.

DESCRIPTION OF THE INVENTION

It is an object of the present invention to overcome the disadvantages of current industrial processes and to disclose a process for the coproduction of long chain ω-amino acids and dibasic acids. In comparison to current industrial processes, the process disclosed in the present invention utilizes mild reaction conditions, provides a high overall yield, and is particularly suitable for industrial production.

The present invention employs long chain keto acid derivatives of the structure (I) as starting materials to coproduce long chain dibasic acids (IV) and ω-amino acids (V), according to the following steps:

(1) Keto acid derivative (I) reacts with hydroxylamine to form oxime derivative (II) or undergoes ammoximation to form oxime (II) in an organic solvent;

(2) Oxime derivative (II) undergoes Beckmann rearrangement to form a mixture of amide derivatives of the structure (IIIa) and (IIIb) in the presence one or more catalysts;

(3) Mixed amide derivatives (IIIa) and (IIIb) are hydrolyzed to yield long chain dibasic acid (IV) and ω-amino acid (V). The hydrolysis of mixed amides also yields a short chain primary alkylamine and a short chain alkanoic acid.

The reaction scheme is as follows:

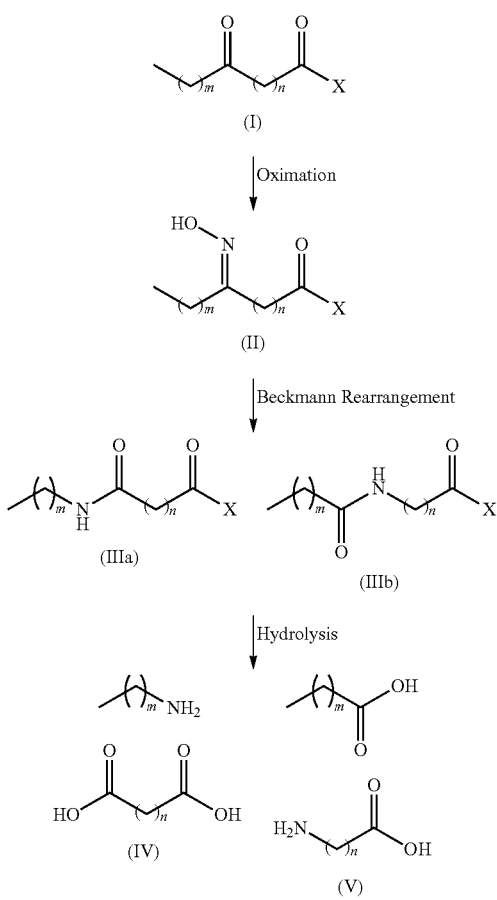

In the reaction scheme, X is OR or $NR_1R_2$; OR is $C_1$-$C_8$ monohydric alcohol or polyhydric alcohols, i.e., ethylene glycol, propanediol, butanediol or glycerol. $R_1$ and $R_2$ are each independently hydrogen and $C_1$-$C_8$ alkyl groups. m is an integral of 0 to 10. n is an integral of 6 to 20. Preferably, X is OR, i.e., keto esters.

It is noted that the starting material is 12-ketostearic acid derivatives, when m=5, n=10. According to the process disclosed in the present invention, the monomer of nylon-11, 11-aminoundecanoic acid is coproduced along with dodecanedioic acid, an important monomer for the production of nylon 612 and nylon 1212.

When m=7, n=8, the starting material is 10-ketostearic acid derivatives. According to the process disclosed in the present invention, 9-aminononanoic acid, the monomer for nylon-9 is coproduced along with sebacic acid, which is used in the production of nylon 610 and nylon 1010.

When m=5, n=12, the starting material is 14-keto arachidic acid derivative. According to the process disclosed in the present invention, 13-aminotridecanoic acid, the monomer for nylon-13, is coproduced along with tetradecanedioic acid (i.e., brassylic acid).

During the formation of oxime derivatives (II), the keto acid derivatives (I), dissolved in an organic solvent, is reacted with aqueous hydroxylamine or is subjected to an ammoximation reaction to form oxime (II). The organic solvent for this reaction can be either water soluble or water insoluble. The requirement for selecting proper solvent is that the solvent can dissolve both the keto derivative (I) and oxime derivative (II), and does not react with starting material, product, and hydroxylamine. For example, aldehydes and ketones as solvents are not suitable for preparing oxime, because the solvents will react with hydroxylamine. Nitriles are also not suitable as the nitrile group can react with hydroxylamine. Amines will react with ketone to form Schiff base and are therefore not suitable solvents. Alcohols can undergo ester exchange reaction with ketoacid derivative (I), thus preferably are not used.

For Beckmann rearrangement, the required solvents have to show good solubility towards both oxime derivative (II) and mixed amide derivatives (III), and can dissolve catalysts for Beckmann rearrangement and will not react with the catalysts.

A solvent for both the oximation and Beckmann rearrangement must be stable and amenable to recover. Different solvents can be used for the oximation reaction or Beckmann rearrangement to satisfy the requirement of each reaction. Preferably, a single solvent is used to satisfy the requirement of both reactions in order to reduce the use and recycling of solvent. More preferably, the selected solvent is not water-soluble so that it can be easily separated after the oximation reaction and Beckmann rearrangement. The amount of solvent used in both reactions is not particularly limited as the solvent only functions to dissolve the reactants and products.

Solvents that show the required properties for both the oximation and Beckmann rearrangement belong to the classes of ester, aliphatics, aromatics, and ethers. Preferable solvents are butyl acetate, ethyl acetate, benzene, toluene, xylene, cumene, anisole, diethyl ether, diisopropyl ether, dibutyl ether, methyl tert-butyl ether, ethyl tert-butyl ether, methyl tetrahydrofuran, petroleum ether, cyclohexane, dichloroethane, methylene chloride, chloroform, carbon tetrachloride, and trifluoromethylbenzene.

A single solvent or a mixture of two or more solvents can be used.

The oximation reaction is carried out at a temperature from 0° C. to 100° C., but can also be carried out at higher temperature under pressure. This reaction is preferably carried out at a temperature from 0° C. to 100° C. under atmospheric pressure. If the temperature is low, the reaction rate is slow, and reaction time is unnecessarily prolonged. Preferably, the reaction temperature is selected to be 60° C. to 80° C.

The oximation reaction is carried out in the air, but can also be carried out under the protection of inert atmosphere, i.e., nitrogen, argon, or helium.

Time for the completion of oximation is related to the reaction temperature, usually in about 0.5 to 24 hours. Preferably, the reaction time is maintained for 1 to 6 hours, and the reaction temperature is controlled at 0° C. to 100° C. If the reaction time is too short, the residual content of ketoacid derivative is too high, the yield will be reduced. Although the residual keto acid derivative can be recovered in the post treatment, additional equipment for recovery will be needed. Prolonged reaction can reduce the residual amount of keto acid derivative, but the volume of reactors becomes unnecessarily large.

Reactor for the oximation can be any reactor conventionally used in the chemical processing, for example, batch stirred reactor, semi-continuous reactor, tubular reactor, or flow reactor. Preferable reactor is continuous stirred tank reactor (CSTR). If CSTR is adopted, aqueous hydroxylamine solution and ketoacid derivative in an organic solvent are simultaneously added in one reactor and then the reaction is completed in a cascade of reactors.

In the oximation reaction, if aqueous solution of hydroxylamine salt is used, such as sulfate or hydrochloride, an alkaline agent, preferably ammonia, is needed to adjust the pH of the reaction solution to a range of 3 to 14 so that the reaction can proceed to completion. After the reaction and separation, the aqueous phase is concentrated to recover ammonium salt, i.e., ammonium sulfate. The oximation reaction can also be carried out by using ammoximation of ketoacid derivative, according to prior art, i.e., hydrogen peroxide and ammonia in the presence of catalyst.

The molar ratio of ketoacid derivative (I) and hydroxylamine can be from 0.1 to 10.0, preferably 1.0 to 2.0, most preferably 1.05 to 1.1 to ensure that ketoacid derivative is completely converted to oxime derivative (II).

After completion of the oximation reaction, oxime derivative (II) remains dissolved in organic phase, and aqueous phase is separated. Although the solubility of water in organic phase is small, but the remaining trace amount of water will destroy the catalytic activity of Beckmann catalyst and must be removed. In order to remove trace amount of water from organic phase, drying agent may be used. Preferably, the remaining water is removed by distilling part of the solvent. The distilled solvent can be used directly in the step of oximation without being dried. After distillation, the residual anhydrous solution of oxime derivative can be directly used for Beckmann rearrangement.

After thorough drying, the oxime derivative (II) is subjected to Beckmann rearrangement to amide derivative (III) by heating in the presence of one or more catalysts. Suitable catalysts are sulfuric acid or activated halogen compounds or a mixture of activated halogen compounds and Lewis acids. Activated halogen compounds can be used for Beckmann rearrangement, but can be used in combination with Lewis acids to achieve better result. Preferably, activated halogen compounds are activated chlorine compounds.

Suitable activated chlorine compounds are thionyl chloride, sulfuryl chloride, chlorosulfonic acid, various sulfonyl chlorides: i.e., methanesulfonyl chloride, toluenesulfonyl chloride, various carbonyl chlorides: i.e., formyl chloride, acetyl chloride, benzoyl chloride, oxalyl chloride, phosgene, diphosgene, triphosgene, boron trichloride, chlorine-containing phosphorus compounds, i.e., phosphorus trichloride, phosphorus pentachloride, oxyphosphoryl chloride, and chlorine-containing heterocycles: i.e., cyanuric chloride, phosphorazine. One or a combination of two or more compounds can be used as catalyst.

Suitable Lewis acids are metal halides, i.e., zinc chloride, ferric chloride, cobalt chloride, stannous chloride, aluminum chloride, titanium chloride, boron trichloride. One or a combination of two or more in any molar ratio can be used.

In the Beckmann rearrangement as described above, activated chlorine-containing compound is used in catalytic amount, i.e., less than 10% of the molar amount of the oxime derivative, preferably in an amount of 0.1 to 5%. As with activated chlorine-containing compound, Lewis acid is also used in catalytic amount, i.e., less than 10% of the molar amount of the oxime derivative, preferably in an amount of 0.1 to 5%.

When sulfuric acid is used in the Beckmann rearrangement, the amount can be determined according to methods known in prior art for Beckmann rearrangement.

The molar ratio of Lewis acid and activated chlorine-containing compound is 1:0.01 to 1:100, preferably between 1:0.3 to 1:1.5.

The amount of catalyst, reaction temperature, reaction pressure, and reaction time are related. Under certain temperature, reaction time can be shortened by increasing the amount of catalyst.

The temperature for the Beckmann rearrangement of oxime derivative is not strictly limited, from room temperature to refluxing temperature. The reaction can also be performed at higher temperature under increased pressure. But if the temperature is too high, the color of rearranged products will darken, rendering post-treatment difficult.

The Beckmann rearrangement can be carried out in atmosphere, but also under inert gases, i.e., nitrogen, argon, or helium as protective atmosphere. This reaction is preferably carried out in dried air. The pressure for carrying out the rearrangement reaction is not limited, from standard normal pressure, to reduced or increased pressure.

The reactor for the Beckmann reaction is not limited. Reactors commonly used in chemical industry, and tubular reactors are suitable. The reaction can be carried out in batch, semi-continuously, or continuously.

After the Beckmann rearrangement, active catalyst may be quenched, but can also be reused after separating off the rearranged products. The active catalyst can be quenched by adding a small amount of water. The added water may also contain small amount of acid, or base, or some inorganic salts.

After the Beckmann rearrangement, the product amide derivative is a mixture of two amides of the structure III(a) and III(b), in an almost equal molar ratio. After recovery of solvent, this mixture can be purified to obtain pure amide derivative before proceeding to a hydrolysis step. On the other hand, crude product of the rearrangement reaction can be directly subjected to hydrolysis, and the impurities can be removed after hydrolysis. In fact, if the purity of oxime ester (II) is good, the rearrangement product is nearly pure.

The hydrolysis of amide derivatives can be carried out with an acid. Suitable acids are sulfuric acid, hydrochloric acid, hydrobromic acid, hydroiodic acid, or nitric acid. One or a combination of two or more acids in any ratio can be used for the hydrolysis reaction. The amount of acid used in hydrolysis reaction and reaction conditions can be determined by those skilled in art. In order to increase the solubility of mixed amide derivatives during the hydrolysis, the reaction system may be added certain organic solvents, i.e., methanol, ethanol, formic acid, acetic acid, et al.

After hydrolysis and cooling crystallization, saturated long chain dibasic acids can be separated. After the mother liquor is neutralized to neutral, long chain ω-amino acid is crystallized and separated. The obtained long chain dibasic acid and ω-amino acid can be purified by recrystallization to yield products of desired quality.

Long chain amide derivatives of the formula III(a) and III(b) can also be hydrolyzed with a base. The amount of base used in the reaction and reaction conditions can be determined by those skilled in art. Suitable base is selected from sodium hydroxide, potassium hydroxide, sodium carbonate, potassium carbonate, and barium hydroxide. One or a combination of two or more bases in any ratio can be used. Solvent for the hydrolysis reaction is water, or an aqueous mixture of organic solvents in any ratio. Suitable organic solvent is selected from the group of methanol, ethanol, isopropanol, tetrahydrofuran, dioxane, et al. One or more solvents in any ratio can be used.

The temperature for the hydrolysis reaction is preferably in the range of 50° C. to 200° C., pressure is preferably from autogenous to increased pressure. The hydrolysis reaction can be carried out in atmosphere, but also under the protection of inert atmosphere.

The time for the hydrolysis reaction is determined by alkali concentration, reaction temperature, from 1 to 24 hours. Preferably the reaction time is from 2 to 4 hours. If the reaction is too short, the hydrolysis is not complete. If the reaction time is too long, the volume of reactor becomes large, necessarily increasing capital investment.

After the hydrolysis, organic solvent if any, is removed. The strongly alkaline pH is neutralized to neutral pH to crystallize long chain ω-amino acid. Suitable acid is selected from one or a combination of two or more acids of sulfuric acid, hydrochloric acid, nitric acid, and organic acids, i.e., formic acid, acetic acid, propionic acid, citric acid, tartaric acid, et al. Preferably, an inorganic acid is selected.

After the separation of long chain ω-amino acid, the pH of the mother liquor is further lowered to a pH of below 5, to precipitate long chain dibasic acid. The product is then separated by solid-liquid separation.

It is particularly important to point out that long chain dibasic acid and long chain co-amino acid produced according to the present invention are of particularly high purity, containing no other long chain dibasic acid, nor long chain imino-dibasic acid.

EXAMPLES

The following examples illustrate the practice of this invention but are not intended to limit its scope.

Example 1. Co-Production of Nylon-11 Monomer and Dodecanedioic Acid 94 g of methyl 12-ketostearate was dissolved in 500 mL of toluene, followed by an aqueous solution of hydroxylamine sulfate (about 8%) containing 13.5 g of hydroxylamine. The mixture was vigorously stirred at 70-85° C., while the pH of the solution was adjusted to 4.5 to 5.0 with aqueous ammonia. After reacting for 6 hours, the starting material was completed transformed to methyl 12-oxime stearate as indicated by HPLC analysis.

After oximation reaction was complete, the mixture was settled to separate off aqueous phase and the organic phase was dried. To the toluene solution were added 1.1 g of cyanuric chloride and 1.5 g of zinc chloride. The solution was stirred for 2 hours at 90-105° C. to complete the Beckmann rearrangement. The reaction was terminated by adding 50 mL of water. The product of mixed amide derivative of an off-white color was obtained after separating aqueous phase and recovering toluene.

The mixed amide derivatives were dissolved in 500 mL of 10% sodium hydroxide, placed in an autoclave, and stirred at 150° C. for 4 hours under autogenous pressure. HPLC analysis indicated that the hydrolysis proceeded to completion.

To the reaction solution were added 500 mL of water, 2 g of activated carbon to decolorize at 90° C. for 30 minutes. After filtration to remove activated carbon, sulfuric acid was added to the filtrate to adjust pH to 7.5. After cooling to room temperature, 11-aminoundecanoic acid crystallized. The solid was filtered, washed extensively with deionized water, and dried to yield 55.8 g of 11-aminoundecanoic acid. HPLC analysis indicated a purity of 99.7%.

The mother liquor was heated to 85° C., acidified with sulfuric acid to a pH of 1, a large amount of solid precipitated. After cooling to room temperature, the solid was separated by filtration, washed with distilled water three times, methanol once. After drying, 62.4 g of dodecanedioic acid was obtained. HPLC analysis indicated a purity of 99.5%.

Example 2. Co-Production of Nylon-9 Monomer and Sebacic Acid 94 g of methyl 10-ketostearate was dissolved in 500 mL of butyl acetate, followed by an aqueous solution of hydroxylamine sulfate (about 8%) containing 12.5 g of hydroxylamine. The mixture was vigorously stirred for 6 hours at 70-80° C., while the pH of the solution was adjusted to 4.5 to 5.0 with aqueous ammonia. HPLC analysis indicated that the starting material was completely transformed to methyl 10-oxime stearate.

After aqueous phase was separated off, 50 mL of butyl acetate was distilled to remove water. The butyl acetate solution was added 0.8 g of triphosgene and 1.2 g of zinc chloride, stirred at 90° C. for 3 hours to complete the Beckmann rearrangement, which was terminated by adding 50 mL of water. The product of mixed amide derivative of an off-white color was obtained after separating aqueous phase and recovering butyl acetate.

The solid material of mixed amide derivatives were dissolved in 200 mL of acetic acid, followed by 200 mL of 30% hydrochloric acid. The solution was refluxed for 48 hours to complete the hydrolysis. To the hot solution was added 500 mL of water. After cooling to room temperature, crystalline material was obtained by filtration and washing with deionized water. 54.6 g of sebacic acid was obtained after drying. HPLC analysis indicated a purity of 99.5%.

The solvent was removed from the mother liquor to a solid residual, which was dissolved in 800 mL of water, and heated to 80° C. To the warm solution was added aqueous ammonia to a pH of 6.5-7.0. After cooling, the precipitated solid was separated by filtration, washed with deionized water, and dried to yield 45.6 g of 9-aminononanoic acid. HPLC analysis indicated a purity of 99.6%.

Example 3. Co-Production of Nylon-13 Monomer and Brassylic Acid 102.2 g of 14-ketoarachidic acid methyl ester was dissolved in 500 mL of anisole, followed by an aqueous solution of hydroxylamine sulfate (about 8%) containing 16.5 g of hydroxylamine. The mixture was vigorously stirred for 8 hours at 75-85° C., while the pH of the solution is adjusted to 4.5 to 5.0 with aqueous ammonia. HPLC analysis indicated that the starting material was completely transformed to methyl ester of 14-oxime arachidic acid.

After aqueous phase was separated off, 50 mL of anisole was distilled to remove water azeotropically. The anisole solution was added 1.2 g of p-toluenesulfonylchloride and 1.5 g of zinc chloride, stirred at 90-105° C. for 2 hours to complete the Beckmann rearrangement, which was terminated by adding 50 mL of water. The product of mixed amide derivatives of an off-white color was obtained after separating aqueous phase and recovering anisole.

The solid material was dissolved in 700 mL of 8% sodium hydroxide, placed into an autoclave and heated to 150° C. for 5 hours to complete the hydrolysis reaction. HPLC showed complete disappearance of the starting material.

To the hydrolysis solution were added 600 mL of water and 2 g of activated carbon. The mixture was stirred at 90° C. for 45 minutes to decolorize. After filtration to remove activated carbon through a pad of cellite, the solution was neutralized with 30% hydrochloric acid at 80-90° C. to a pH of 7.0-7.5. After the mixture was cooled to room temperature, the precipitated solid was separated by filtration, washed with deionized water, dried to yield 62.7 g of 13-aminotridecanoic acid. HPLC analysis indicated a purity of 99.5%.

The mother liquor was heated to 85° C., acidified with 30% hydrochloric acid to a pH of 1 to obtain a precipitate. After cooling to room temperature, the precipitated solid was separated by filtration, washed with deionized water, then with methanol, finally dried to yield 70.6 g of brassylic acid. HPLC analysis indicated a purity of 99.7%.

Example 4. Ammoximation of Methyl 12-Ketostearate 95 g of methyl 12-ketostearate was dissolved in 500 mL of toluene, followed by 20 g of TS-1 catalyst. The mixture was vigorously stirred at 70° C., while 50 mL of 27.5% hydrogen peroxide and 70 mL of 25% ammonia were added slowly at the same time. The stirring was continued for an additional 60 minutes at 75° C. after the addition of hydrogen peroxide and ammonia. HPLC analysis showed a complete conversion of starting material to methyl 12-oxime stearate. Following the procedure in Example 1, 28.2 g of 11-aminoundecanoic acid was obtained with a purity of 99.5%, as assayed by HPLC analysis. In addition, 31.9 g of dodecanedioic acid was obtained with a purity of 99.3%, as assayed by HPLC analysis.

Example 5. Sulfuric Acid Catalyzed Beckmann Rearrangement of Methyl 12-Oximestearate To 100 mL of 98% sulfuric acid was added slowly 30 g of methyl 12-oxime stearate, which was prepared according to procedure described in Example 1 and which has a purity of 99.2%. The solution was slowly heated to 100° C., and maintained at the same temperature for 1 hour. Afterwards, the solution was poured to 200 g of ice and stirred to yield 28 g of mixed amide derivative. Following the procedure in Example 1, 8.9 g of 11-aminoundecanoic acid was obtained with a purity of 99.2%, as assayed by HPLC analysis. In addition, 9.6 g of dodecanedioic acid was obtained with a purity of 99.4%, as assayed by HPLC analysis.

It will be understood that the foregoing examples, explanation, and drawings are for illustrative purpose only and that in view of the instant disclosure various modifications of the present invention will be self-evident to those skilled in the art and are to be included within the spirit and purview of this application and the scope of the appended claims.

What is claimed is:

1. A process for the co-production of long chain ω-amino acid of formula (V) and long chain dibasic acid of formula (IV), comprising:
   (1) reacting the ketoacid derivative (I) of the formula:

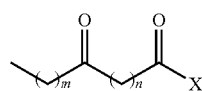
   (I)

in a solvent with hydroxylamine or subjecting the ketoacid derivative (I) in a solvent to ammoximation to produce oxime acid derivative (II) of the formula:

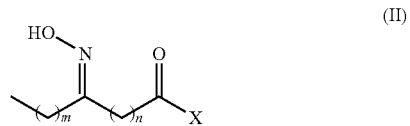
   (II)

wherein X is OR or $NR_1R_2$, wherein OR is $C_1$-$C_8$ monohydric alcohol or polyhydric alcohol, $R_1$ and $R_2$ are each independently hydrogen or $C_1$-$C_8$ alkyl group, m is an integral from 0 to 10, n is an integral from 6 to 20;
   (2) subjecting the oxime derivative (II) in a solvent to Beckmann rearrangement to yield a mixture of amide derivatives (IIIa) and (IIIb)

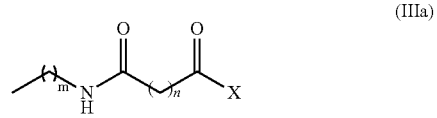
   (IIIa)

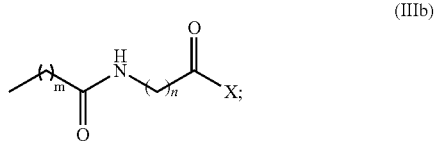
   (IIIb)

and
   (3) hydrolyzing the mixed amide derivatives to long chain ω-amino acid (V) and long chain dibasic acid (IV)

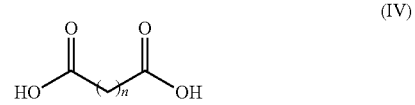
   (IV)

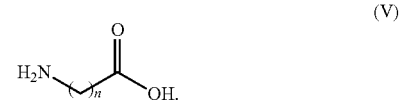
   (V)

2. The process according to claim 1, wherein the temperature for oximation is maintained from 0° C. to 100° C., and the pH is in a range of 3 to 14.

3. The process according to claim 1, wherein catalyst for the Beckmann rearrangement of step (2) is sulfuric acid, an activated chlorine-containing compound, or a mixture of a Lewis acid and an activated chlorine-containing compound.

4. The process according to claim 1, wherein the solvent for oximation, ammoximation, and Beckmann rearrangement is the same or a different solvent.

5. The process according to claim 1, wherein the mixed amide derivatives are hydrolyzed by an acid or a mixture of acids to produce long chain ω-amino acid (V) and long chain dibasic acid (IV).

6. The process according to claim 1, wherein the mixed amide derivatives are hydrolyzed by a base or a mixture of bases to produce long chain ω-amino acid (V) and long chain dibasic acid (IV).

7. The process according to claim 1, wherein long chain ω-amino acid (V) and long chain dibasic acid (IV) are separated from their mixture by a stepwise neutralization.

8. The process according to claim 1, wherein long chain ω-amino acids of the formula (V) are 9-aminononanoic acid, 11-aminoundecanoic acid, and 13-aminotridecanoic acid.

9. The process according to claim 1, wherein long chain dibasic acids of the formula (IV) are sebacic acid, dodecanedioic acid, and brassylic acid.

10. The process according to claim 1, wherein polyhydric alcohol is selected from ethylene glycol, propylene glycol, butanediol, or glycerol.

\* \* \* \* \*